United States Patent
Gayser, Jr. et al.

(10) Patent No.: US 6,884,288 B2
(45) Date of Patent: Apr. 26, 2005

(54) DRY-POWDER FILM COATING COMPOSITION AND METHOD OF PREPARATION

(75) Inventors: Charles W. Gayser, Jr., Harriman, NY (US); Jean-Paul Goyette, Canterbury, CT (US)

(73) Assignee: Chr. Hansen, Inc., Milwaukee, WI (US)

( * ) Notice: Subject to any disclaimer, the term of this patent is extended or adjusted under 35 U.S.C. 154(b) by 0 days.

(21) Appl. No.: 10/706,194

(22) Filed: Nov. 12, 2003

(65) Prior Publication Data

US 2004/0096503 A1 May 20, 2004

Related U.S. Application Data

(63) Continuation of application No. 09/656,082, filed on Sep. 6, 2000, now Pat. No. 6,660,302.

(51) Int. Cl.$^7$ .................... C09D 101/00; C09D 101/28; C09D 105/00; A61K 9/14; A61K 9/16; A61K 9/50

(52) U.S. Cl. ................ 106/162.8; 106/162.9; 426/302; 426/615; 424/480; 424/488; 424/489; 424/490; 424/491

(58) Field of Search .................... 106/162.8, 162.9; 426/302, 615; 424/480, 488, 489, 490, 491

(56) References Cited

U.S. PATENT DOCUMENTS

| | | | | | |
|---|---|---|---|---|---|
| 3,406,031 | A | * | 10/1968 | Lee | 106/162.8 |
| 3,413,400 | A | * | 11/1968 | Lee | 514/777 |
| 4,750,938 | A | * | 6/1988 | Cottrell | 106/146.5 |
| 5,308,647 | A | * | 5/1994 | Lappi | 427/154 |
| 5,591,455 | A | * | 1/1997 | Signorino | 424/490 |
| 6,660,302 | B1 | * | 12/2003 | Gayser et al. | 424/489 |

FOREIGN PATENT DOCUMENTS

| | | |
|---|---|---|
| DE | 2614020 | 10/1977 |
| WO | WO 91/15548 | 10/1991 |
| WO | WO 99/03449 | 1/1999 |

* cited by examiner

*Primary Examiner*—David Brunsman
(74) *Attorney, Agent, or Firm*—Godfrey & Kahn, S.C.

(57) ABSTRACT

An edible dry-powder formulation of a film coating for pharmaceuticals and confectioneries using gum acacia as a low-cost film former is provided. A cellulosic polymer such as hydroxypropyl methylcellulose is used in addition to the gum acacia. A plasticizer such as propylene glycol is also added. The resulting formulation is a dry, free flowing powder that can be put into solution and applied to a tablet or other substrate without an extended waiting period. The resulting film coating is clear, shiny, durable and extremely economical. Because the formulation is a dry powder, it has along shelf life and low shipping costs.

14 Claims, No Drawings

DRY-POWDER FILM COATING COMPOSITION AND METHOD OF PREPARATION

CROSS-REFERENCE TO RELATED APPLICATION

This application is a continuation of application Ser. No. 09/656,082, filed Sep. 6, 2000, now U.S. Pat. No. 6,660,302 which is specifically incorporated herein by reference in its entirety for all purposes.

FIELD OF THE INVENTION

This invention relates generally to a film coating compositions and methods and more particularly to an edible dry-powder film coating composition and method for coating pharmaceuticals and confectionaries.

BACKGROUND OF THE INVENTION

Cellulose polymers such as hydroxypropyl methylcellulose ("HPMC") have long been recognized in the art as suitable aqueous film coatings for pharmaceutical tablets and the like. While it is common to use HPMC (and other similar polymers), it can be rather expensive. The available alternative for a non-enteric coating is a sugar coating. Though a sugar coating can be less expensive, can prevent moisture migration into the tablet substrate and can mask bad flavors, it is not as desirable as a film coating for all uses. For example, sugar coatings cannot be applied as thinly as a film coating, are not clear, and are not non-caloric. Furthermore, sugar coatings have a higher risk of cracking than do film coatings. Finally, sugar coatings are typically mixed with hot water prior to application, which is not always readily available.

Manufacturers faced with the need to provide a durable, virtually non-caloric, thin or clear coat on tablets or confectionaries must pay a relatively high amount per pound for HPMC, or live with the drawbacks of sugar coatings.

U.S. Pat. No. 5,591,455 to Signorino suggests using gum acacia, instead of or in addition to other ingredients, in combination with HPMC to make a "wet-powder" blend for aqueous film coating. Water and plasticizers are added to the wet-powder blend prior to application. However, there is no disclosure of the amount of gum acacia that is effective. This failure is critical since gum acacia has not previously been used as a film-former, and would not ordinarily be expected to be used as a film former. This is because gum acacia is traditionally used as a wetting agent, emulsifier or binder—applications that are markedly different from those in which film formers are generally used. Moreover, wet powder products, such as that disclosed in the Signorino patent, contains up to 30% water resulting in a heavier product that is significantly more costly to ship. In addition, the added moisture often negatively affects the shelf life of the blended ingredients (e.g., wet gum acacia can readily become moldy).

U.S. Pat. No. 5,470,581 to Grillo et al. discloses a dry-powder edible film-coating composition for use on pharmaceuticals and the like, comprising a dry mixture of a cellulosic polymer, maltodextrin and a plasticizer. The maltodextrin is used in quantities ranging from 5% to 78.5% by weight of the powder. Though maltodextrin is a film former that costs less than those generally used, i.e. hydroxypropyl methylcellulose, it does not perform as well because it yields a brittle coating that is prone to cracking.

Futhermore, U.S. Pat. No. 4,453,370 to Porter et al. discloses another dry-powder edible film-coating composition for use on pharmaceuticals and the like, comprising in part of powdered particles of a film forming non-toxic edible polymer and a pigment. However, the resulting film coating is not clear.

Therefore, there remains a need for a less-expensive, dry-powder film coating for pharmaceuticals and confectionaries that is clear and performs as well as a coating containing more expensive components.

SUMMARY OF THE INVENTION

Therefore, it is an object of the present invention to provide a film coating for pharmaceuticals and confectionaries that costs less that presently available film coatings.

It is a further object of the present invention to provide a film coating for pharmaceuticals and confectionaries that is durable.

It is yet another object of the present invention to provide a film coating for pharmaceuticals and confectionaries that does not contain added water prior to being put into solution for application to a substrate.

It is still another object of the present invention to provide a film coating for pharmaceuticals and confectionaries that is clear, shiny, and has defined logo resolution.

It is a still further object of the present invention to provide a film coating for pharmaceuticals and confectionaries that is easy to apply, and does not require mixing with hot water prior to application.

These objects, and other aspects and advantages of the present invention are achieved by using gum acacia as a film former in addition to a cellulosic film former such as hydroxypropyl methylcellulose and a plasticizer such as propylene glycol in a dry powder form.

Gum acacia (*Acacia seyal*) has been used commercially in the United States since the late 1980's, and is also available as gum arabic, kordofan gum, senegal gum, indian gum, and cape gum. Prior to this time, the significant use of gum acacia occurred in India in a raw state as a confection. Subsequent to the approval of gum acacia as a pharmaceutical ingredient by the FDA, its use and importance has increased significantly. However, gum acacia is traditionally used as a wetting or thickening agent, as an emulsifier, or as a binder. Specifically, gum acacia has been used for compounding pills, lozenges, mixtures, and emulsions; and for administering insoluble substances in water, as oils, resins, balsams, camphor, musk, etc. Though gum acacia does not deteriorate if kept dry, if put into solution (i.e. a concentrated mucilage) it will sour after an extended period. Hot water hastens this fermentation, if employed in making a mucilage or the like. Further, dilute solutions of the gum become moldy.

In one embodiment of the present invention, the cellulosic polymer is added to the composition in a range of about zero percent (0%) to about ninety percent (90%) by weight of the composition, the gum acacia is added to the composition in a range of about five percent (5%) to about ninety percent (90%) by weight of the composition, and the plasticizer is added to the composition in a range of about zero percent (0%) to about fifteen percent (15%) by weight of the composition.

Other embodiments of the present invention include a detackifier such as talc or magnesium stearate.

In a method in accordance with the present invention, a dry powder film forming composition is made by mixing dry ingredients gum acacia, a cellulosic polymer, and a plasticizer in a blender until thoroughly mixed. Then, just prior to use, the dry powder can be put into solution by bringing about one-half the required amount of water to boiling, adding the dry powder of the present invention under agitation, and bringing the solution to a desired concentration by adding cold water. The solution is stirred until completely dissolved, and the solution brought to a temperature of about 23° C. The solution is measured until a flash point of 93.3° C. (200° F.) is obtained.

The present invention offers two substantial benefits over the prior art. First, the present invention offers a reduction in cost in excess of 10% when compared to the widely used pigmented coating systems. Second, the present invention offers the flexibility of either providing a pigmented or clear coat. In addition, the composition in the present invention is able to offer: (1) rapid dissolution in water; (2) minimum generation of foam; (3) superior film quality; (4) good substrate adhesion including edges and logos; (5) defined logo resolution; (6) translucent film with brilliant shine; (7) ideal tensile strength and elasticity; (7) simplified coating formulation; and (8) ease of application. Many traditional formulations of pigmented coating systems are able to provide many of these qualities; however, rarely are do those formulations provide a clear coat at a cost reduction in excess of 10%.

DETAILED DESCRIPTION

The present invention is a dry powder generally comprising gum acacia, a cellulosic polymer and plasticizers, whereby the dry powder can be used in an aqueous solution for application as an edible coating for tablets, capsules, confectionaries and the like.

The most preferred embodiment of this invention combines a substantial amount of gum acacia and hydroxypropyl methylcellulose ("HPMC") in a dry powder to deliver a highly cost-effective film-forming polymer. Though traditionally used as a wetting agent or adhesive, the gum acacia functions as a film former when combined with a cellulosic polymer such as HPMC. The film-forming polymers are combined with plasticizers such as polyethylene glycol to increase the elasticity of the resulting film coating.

The exact proportions of the gum acacia and HPMC in the present invention are not critical, although the most preferred embodiment of the composition is as follows: (1) HPMC 6 centipoise (hereinafter "cps"), (25.0% by weight); HPMC 15 cps, (20.0% by weight); gum acacia, (45.0% by weight); polyethylene glycol 400, (5.0% by weight); and polyethylene glycol 8,000, (5.0% by weight). Preferably, the gum acacia is obtained in powder form from Colloides Naturels International, as Gum Arabic (Spray Gum AS).

Thus the preferred embodiment, when applied to tablet substrates such as vitamins and dietary supplements, provides optimum physical characteristics as well as a substantial reduction in production costs. In contrast to the widely available pigmented coatings, the clear coat of the present invention exhibits comparable physical properties, such as elasticity, tensile strength and crushing strength. Significantly, the coating supports the evaporation of moisture off-of the surface of the substrate, rather than the migration of moisture into the core of the substrate.

Alternative embodiments of the present invention are shown below in Table 1. When gum acacia is added to a given formulation so that it is more than about 60% by weight of the dry powder composition, tackiness of the resulting film coating can occur. Therefore, detackifiers such as magnesium stearate and talc may be added to the composition when deemed desirable. Furthermore, maltodextrin or starch can be added as additional polymer film formers. However, the polymers maltodextrin and starch, and the detackifier talc will yield a film that is less translucent than other formulations that do not contain these components.

TABLE 1

| COMPONENT | COMPONENT FUNCTION | PREFERRED RANGE (% BY WEIGHT) | MOST PREFERRED RANGE (% BY WEIGHT) |
|---|---|---|---|
| Gum Acacia | Polymer/Film former | 5.0–90.0% | 5.0–60.0% |
| Hydroxypropyl methylcellulose 3 cps | Polymer/Film former | 0.0–90.0% | 0.0–60.0% |
| Hydroxypropyl methylcellulose 6 cps | Polymer/Film former | 0.0–90.0% | 0.0–60.0% |
| Hydroxypropyl methylcellulose 15 cps | Polymer/Film former | 0.0–90.0% | 0.0–30.0% |
| Hydroxypropyl methylcellulose 50 cps | Polymer/Film former | 0.0–90.0% | 0.0–15.0% |
| Methylcellulose 15 cps | Polymer/Film former | 0.0–90.0% | 0.0–30.0% |
| Maltodextrin M-180 | Polymer/Film former | 0.0–5.0% | 0.0–5.0% |
| Starch | Polymer/Film former | 0.0–90.0% | 0.0–25.0% |
| Polyethylene glycol 400 | Plasticizer | 0.0–15.0% | 0.0–10.0% |
| Polyethylene glycol 3,350 | Plasticizer | 0.0–15.0% | 0.0–15.0% |
| Polyethylene glycol 8,000 | Plasticizer | 0.0–15.0% | 0.0–15.0% |
| Triacetin | Plasticizer | 0.0–15.0% | 0.0–10.0% |
| Glycerine | Plasticizer | 0.0–15.0% | 0.0–10.0% |
| Triethyl Citrate | Plasticizer | 0.0–15.0% | 0.0–10.0% |
| Magnesium Stearate | Detackifier | 0.0–15.0% | 0.0–5.0% |
| Talc | Detackifier | 0.0–50.0% | 0.0–25.0% |

In addition to the components listed in Table 1, other edible plasticizers, cellulosic polymers, and detackifiers can be used. For example, other plasticizers include propylene glycol, mineral oil, monoglycerides, dibutyl sebecate, acetyltriethylcitrate, acetyltributylcitrate, acetylated monoglyceride, hydroxylated lecithin or the like. Other cellulosic polymers include hydroxypropyl cellulose, hydroxyethylcellulose, hydroxyethyl methylcellulose, carboxymethylcellulose, polyvinyl alcohol or the like. Other detackifiers include hydroxylated lecithin, stearic acid, hydrogenated vegetable oil, silica and wax. Detackifiers prevent coated tablets and the like from sticking together.

Pigments such as titanium dioxide, FD&C aluminum lakes, natural colorants, synthetic oxides or the like may also be used with any of the formulations, but can negatively affect the coating clarity. Preferably, pigments are added to the final formulation so that the colored formulation contains pigment of up to about 25% by weight.

The following examples illustrate various formulations of the present invention (all percentages are by weight):

EXAMPLE 1

| | |
|---|---|
| Gum Acacia | 35.0% |
| Hydroxypropyl methylcellulose 6 cps | 45.0% |
| Hydroxypropyl methylcellulose 15 cps | 10.0% |
| Polyethylene glycol 400 | 1.0% |

| -continued | |
|---|---|
| Polyethylene glycol 8,000 | 9.0% |
| EXAMPLE 2 | |
| Gum Acacia | 25.0% |
| Hydroxypropyl methylcellulose 6 cps | 64.0% |
| Hydroxypropyl methylcellulose 15 cps | 1.0% |
| Polyethylene glycol 400 | 9.0% |
| Polyethylene glycol 8,000 | 1.0% |
| EXAMPLE 3 | |
| Gum Acacia | 45.0% |
| Hydroxypropyl methylcellulose 6 cps | 25.0% |
| Hydroxypropyl methylcellulose 15 cps | 10.0% |
| Talc | 10.0% |
| Polyethylene glycol 400 | 5.0% |
| Polyethylene glycol 8,000 | 5.0% |
| EXAMPLE 4 | |
| Gum Acacia | 45.0% |
| Hydroxypropyl methylcellulose 6 cps | 25.0% |
| Hydroxypropyl methylcellulose 15 cps | 10.0% |
| Maltodextrin M-180 | 10.0% |
| Polyethylene glycol 400 | 5.0% |
| Polyethylene glycol 8,000 | 5.0% |
| EXAMPLE 5 | |
| Gum Acacia | 45.0% |
| Hydroxypropyl methylcellulose 6 cps | 25.0% |
| Hydroxypropyl methylcellulose 15 cps | 10.0% |
| Starch | 10.0% |
| Polyethylene glycol 400 | 5.0% |
| Polyethylene glycol 8,000 | 5.0% |
| EXAMPLE 6 | |
| Gum Acacia | 45.0% |
| Hydroxypropyl methylcellulose 6 cps | 30.0% |
| Hydroxypropyl methylcellulose 15 cps | 15.0% |
| Triacetin | 5.0% |
| Polyethylene glycol 8,000 | 5.0% |
| EXAMPLE 7 | |
| Gum Acacia | 45.0% |
| Hydroxypropyl methylcellulose 6 cps | 30.0% |
| Hydroxypropyl methylcellulose 15 cps | 15.0% |
| Glycerine | 5.0% |
| Polyethylene glycol 8,000 | 5.0% |
| EXAMPLE 8 | |
| Gum Acacia | 45.0% |
| Hydroxypropyl methylcellulose 6 cps | 30.0% |
| Hydroxypropyl methylcellulose 15 cps | 15.0% |
| Triethyl Citrate | 5.0% |
| Polyethylene glycol 8,000 | 5.0% |
| EXAMPLE 9 | |
| Gum Acacia | 45.0% |
| Hydroxypropyl methylcellulose 6 cps | 30.0% |
| Hydroxypropyl methylcellulose 15 cps | 14.0% |
| Polyethylene glycol 400 | 5.0% |
| Polyethylene glycol 8,000 | 5.0% |
| Magnesium Stearate | 1.0% |

In the following examples, methylcellulose is substituted for HPMC.

| EXAMPLE 10 | |
|---|---|
| Gum Acacia | 45.0% |
| Methylcellulose 15 cps | 45.0% |
| Polyethylene glycol 400 | 5.0% |
| Polyethylene glycol 8,000 | 5.0% |
| EXAMPLE 11 | |
| Gum Acacia | 45.0% |
| Methylcellulose 15 cps | 45.0% |

| -continued | |
|---|---|
| Glycerine | 10.0% |
| EXAMPLE 12 | |
| Gum Acacia | 45.0% |
| Methylcellulose 15 cps | 45.0% |
| Triacetin | 10.0% |

Method of Preparation

The desired components of the present invention are blended as a dry powder in accordance with conventional practice. Preferably, components having the highest volume are added to the blending equipment prior to components having a relatively lesser volume. Such preparation will yield a free flowing, off-white powder that is water-soluble or water dispersible. When this dry powder is put into solution or suspension, it may be applied to tablets or the like. without having to wait several hours prior to application.

In the practice of the present invention, the preparation of a solution that can be used for quality control purposes proceeds as follows: (1) bring about one-half of the required amount of water to boiling (the required amount dependant on desired viscosity and formulation); (2) add the dry powder of the present invention under agitation until thoroughly wetted (optionally, pigments may be added after the dry powder); (3) bring to desired concentration with cold water; (4) stir until completely dissolved; (5) adjust the temperature of the solution to 23° C.; and (6) measure the solution until a flash point reading of 93.3° C. (200F.) is obtained.

In the practice of the present invention, the preparation of a solution that can be used for coating tablets or the like proceeds as follows: (1) mix water to the dry-powder composition of the present invention to obtain a ten percent (10%) solution; (2) let the solution stand for about 30 minutes; and (3) spray the solution onto the substrate. It is not necessary to heat the water. Therefore, cold water can be used.

When dissolved in water, the composition yields a clear solution for aqueous film coating with a low viscosity. In particular, when in solution, the preferred embodiment's viscosity ranges from 75–150 cps when measured by the Brookfield Small Chamber Method (Model RVTD) (10% w/w in water, USP; Chamber 13R; Spindle #21; 100 RPM; 23° C.). Viscosity is directly affected by the amount of water added to the solution, and the required amount of water will vary depending on the formulation of the present invention.

The film-forming compositions of the invention are not prone to settling or other breakdowns. Further, it is believed that such compositions remain free from bacterial formation. The shelf life of this product is three years when stored in tight containers in the absence of excessive heat and/or moisture. Polyethylene-lined drums are acceptable packaging.

Although the invention has been herein shown and described in what is conceived to be the most practical and preferred embodiment, it is recognized that departures may be made therefrom within the scope of the invention which is not to be limited to the illustrative details disclosed.

We claim:

1. A dry powder film forming composition for use in coating pharmaceutical tablets, food, and confectionery products, comprising:

a film forming agent including a powdered cellulosic polymer and gum acacia; and a powdered edible plasticizer, wherein the composition is capable of forming an aqueous solution having a low viscosity ranging from about 75 to about 150 cps when measured by the Brookfield Small Chamber Method (10% w/w in water, USP; Model RVTD; Chamber 13R; Spindle #21; 100 rpm; 23° C.).

2. The dry powder film forming composition of claim 1, wherein said powdered cellulosic polymer is selected from the group consisting of hydroxypropyl methylcellulose, methylcellulose, hydroxyethyl methylcellulose, hydroxypropyl cellulose, or carboxymethyl cellulose.

3. The dry powder film forming composition of claim 1, wherein said gum acacia is selected from the group consisting of gum arabic, kordofan gum, senegal gum, indian gum, and cape gum.

4. The dry powder film forming composition of claim 1, wherein said edible plasticizer is selected from the group consisting of polyethylene glycol, propylene glycol, glycerin, triacetin, triethyl citrate, acetyltriethylcitrate, acetyltributylcitrate, or acetylated monoglyceride, mineral oil, monoglycerides and dibutyl seberate.

5. A method of making an aqueous solution for film coating pharmaceutical tablets, food, or confectionary products, comprising the steps of:

mixing water and a dry powder film coating composition according to claim 1 to form an aqueous solution having a low viscosity ranging from about 75 to about 150 cps when measured by the Brookfield Small Chamber Method (10% w/w in water, USP; Model RVTD; Chamber 13R; Spindle #21; 100 RPM; 23° C.).

6. A method of film coating pharmaceutical tablets, food, or confectionary products, comprising the steps of:

spraying an aqueous solution formed according to the method of claim 5 onto pharmaceutical tablets, food, or confectionary products.

7. A dry powder film forming composition for use in coating pharmaceutical tablets, food, and confectionery products, comprising:

a film forming agent including a powdered cellulosic polymer and gum acacia;

a powdered edible plasticizer; and a detackifier, where the composition is capable of forming an aqueous solution having a low viscosity ranging from about 75 to about 150 cps when measured by the Brookfield Small Chamber Method (10% w/w in water, USP; Model RVTD; Chamber 13R; Spindle #21; 100 rpm; 23° C.).

8. A dry powder film forming composition of claim 7, wherein said powdered cellulosic polymer is selected from the group consisting of hydroxypropyl methylcellulose, methylcellulose, hydroxyethyl methylcellulose, hydroxypropyl cellulose, or carboxymethyl cellulose.

9. A dry powder film forming composition of claim 7, wherein said gum acacia is selected from the group consisting of gum arabic, kordofan gum, senegal gum, indian gum, and cape gum.

10. The dry powder film forming composition of claim 7, wherein said edible plasticizer is selected from the group consisting of polyethylene glycol, propylene glycol, glycerin, triacetin, triethyl citrate, acetyltriethylcitrate, acetyltributylcitrate, or acetylated monoglyceride, mineral oil, monoglycerides and dibutyl seberate.

11. The dry powder film forming composition of claim 7, wherein said detackifier is selected from the group consisting of talc, hydrogenated vegetable oils, silica, and waxes, magnesium stearate, lecithin and stearic acid.

12. The dry powder film forming composition of claim 7, wherein the amount of said cellulosic polymer in said composition is in the range of about zero percent (0%) to about ninety percent (90%) by weight of the composition.

13. The dry powder film forming composition of claim 7, wherein the amount of said gum acacia in said composition is in the range of about five percent (5%) to about ninety percent (90%) by weight of the composition.

14. The dry powder film forming composition of claim 7, wherein the amount of said plasticizer in said composition is in the range of about zero percent (0%) to about fifteen percent (15%) by weight of the composition.

* * * * *